US009927362B2

(12) United States Patent
Kumar et al.

(10) Patent No.: US 9,927,362 B2
(45) Date of Patent: Mar. 27, 2018

(54) SYSTEM AND METHOD FOR TOMOGRAPHIC LIFETIME MULTIPLEXING

(71) Applicant: THE GENERAL HOSPITAL CORPORATION, Boston, MA (US)

(72) Inventors: Anand T. Kumar, Arlington, MA (US); Steven S. Hou, Malden, MA (US)

(73) Assignee: THE GENERAL HOSPITAL CORPORATION, Boston, MA (US)

( * ) Notice: Subject to any disclaimer, the term of this patent is extended or adjusted under 35 U.S.C. 154(b) by 0 days.

(21) Appl. No.: 15/118,529

(22) PCT Filed: Feb. 13, 2015

(86) PCT No.: PCT/US2015/015846
§ 371 (c)(1),
(2) Date: Aug. 12, 2016

(87) PCT Pub. No.: WO2015/134176
PCT Pub. Date: Sep. 11, 2015

(65) Prior Publication Data
US 2017/0052119 A1 Feb. 23, 2017

Related U.S. Application Data

(60) Provisional application No. 61/939,941, filed on Feb. 14, 2014.

(51) Int. Cl.
*G01N 21/64* (2006.01)

(52) U.S. Cl.
CPC .......... *G01N 21/6408* (2013.01); *G01N 2201/06113* (2013.01)

(58) Field of Classification Search
CPC .................................. G01N 21/6408
See application file for complete search history.

(56) References Cited

U.S. PATENT DOCUMENTS

| 8,570,507 B1 | 10/2013 | Cooper et al. |
| 2009/0164130 A1 | 6/2009 | Kumar et al. |
| 2012/0153187 A1* | 6/2012 | Laidevant ............ A61B 5/0073 250/459.1 |

OTHER PUBLICATIONS

Arridge, et al., Optical Tomography: Forward and Inverse Problems, Inverse Problems, 2009, 25(12):123010, 69 pages.
(Continued)

*Primary Examiner* — David Porta
*Assistant Examiner* — Hugh H Maupin
(74) *Attorney, Agent, or Firm* — Yakov S. Sidorin; Quarles & Brady LLP

(57) ABSTRACT

System and method for optical tomographic imaging optimizing analysis of time-domain data as a result of combination of lifetime multiplexing of low-cross-talk asymptotic photons with highly spatially resolved early photons. The tomographic data reconstruction employs a decay amplitude-based asymptotic approach and a matrix equation with a weight matrix that includes two different portions respectively representing time domain sensitivity functions and continuous-tomography weight matrices. System may employ a lifetime fluorescent tomography imaging system.

19 Claims, 11 Drawing Sheets

(56) References Cited

OTHER PUBLICATIONS

Bertero, et al., Introduction to Inverse Problems in Imaging, Copyright IOP Publishing 1998, pp. vii-ix, 98-136 and 299-302.

Boas, et al., Three Dimensional Monte Carlo Code for Photon Migration Through Complex Heterogeneous Media Including the Adult Human Head, Optics Express, 2002, 10(3):159-170.

Byrd, et al., A Limited Memory Algorithm for Bound Constrained Optimization, SIAM Journal on Scientific Computing, 1995, 16(5):1190-1208.

Chen, et al., Monte Carlo Based Method for Fluorescence Tomographic Imaging with Lifetime Multiplexing Using Time Gates, Biomedical Optics Express, 2011, 2(4):871-886.

Gao, et al., A Linear, Featured-Data Scheme for Image Reconstruction in Time-Domain Fluorescence Molecular Tomography, Optics Express, 2006, 14(16):7109-7124.

Holt, et al., Multiple-Gate Time Domain Diffuse Fluorescence Tomography Allows More Sparse Tissue Sampling Without Compromising Image Quality, Optics Letters, 2012, 37(13):2559-2561.

Kumar, et al., Fluorescence-Lifetime-Based Tomography for Turbid Media, Optics Letters, 2005, 30(24):3347-3349.

Kumar, et al., A Time Domain Fluorescence Tomography System for Small Animal Imaging, IEEE Trans. Med. Imaging, 2008, 27(8):1152-1163.

Lam, et al., Time Domain Fluorescent Diffuse Optical Tomography: Analytical Expressions, Optics Express, 2005, 13 (7):2263-2275.

Niedre, et al., Early Photon Tomography Allows Fluorescence Detection of Lung Carcinomas and Disease Progression in Mice in Vivo, PNAS, 2008, 105(49):19126-19131.

Raymond, et al., Lifetime-Based Tomographic Multiplexing, Journal of Biomedical Optics, 2010, 15(4):x46011-1 thru 046011-9.

Rice, et al., Resolution Below the Point Spread Function for Diffuse Optical Imaging Using Fluorescence Lifetime Multiplexing, Optics Letters, 2013, 38(12)2038-2040.

Wu, et al., Fluorescence Tomographic Imaging in Turbid Media Using Early-Arriving Photons and Laplace Transforms, Proc. Natl. Acad. Sci. USA, 1997, 94:8783-8788.

International Search Report and Written Opinion dated May 27, 2015 in connection with PCT/US2015/015846.

Kumar, A. et al. "Time Resolved Fluorescence Tomography of Turbid Media Based on Lifetime Constrast" Opt. Express, 14(25): 12255-12270, Dec. 11, 2006 {retrieved from the Internet: Apr. 22, 2015] URL: http://www.ncbi.nlm.nih.gov/pmc/articles/PMC2700299/.

\* cited by examiner

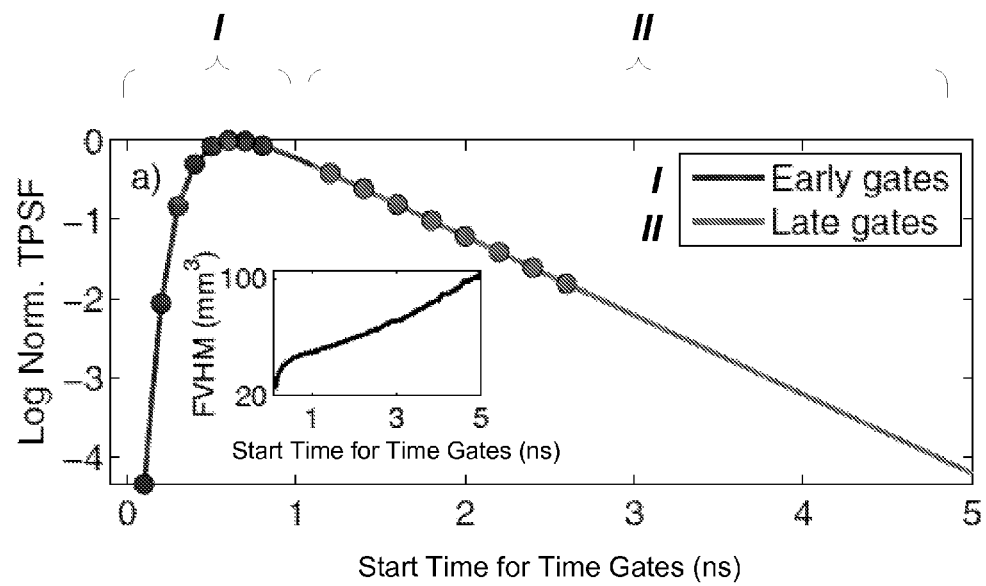
FIG. 1A
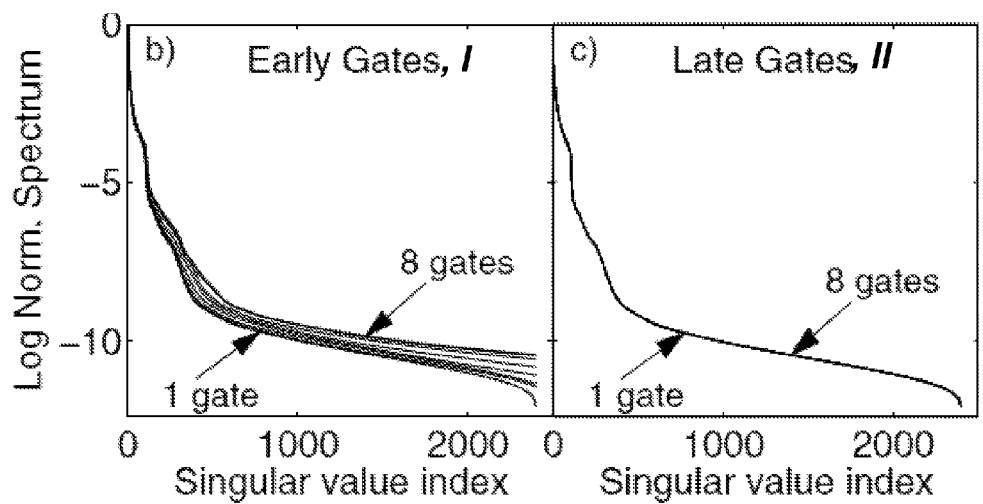
FIG. 1B
FIG. 1C

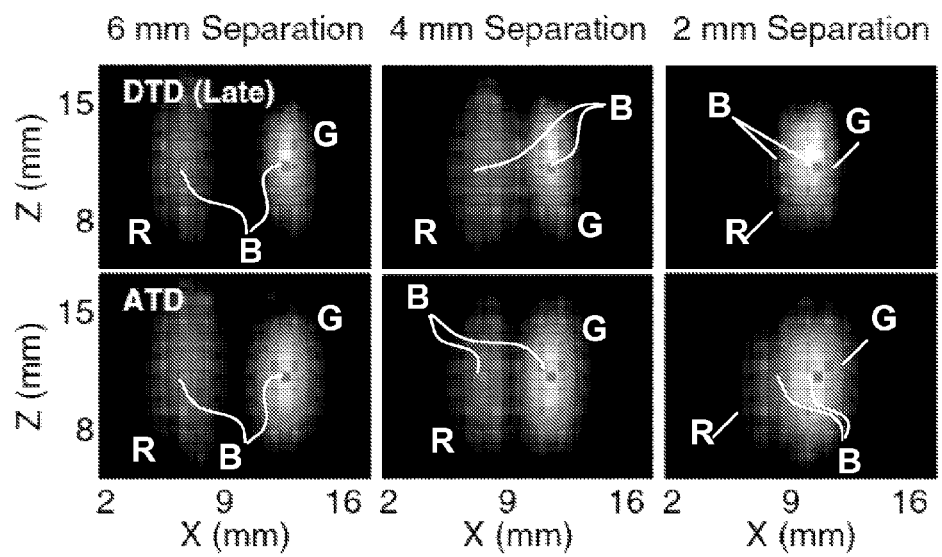
FIG. 2A
FIG. 2B
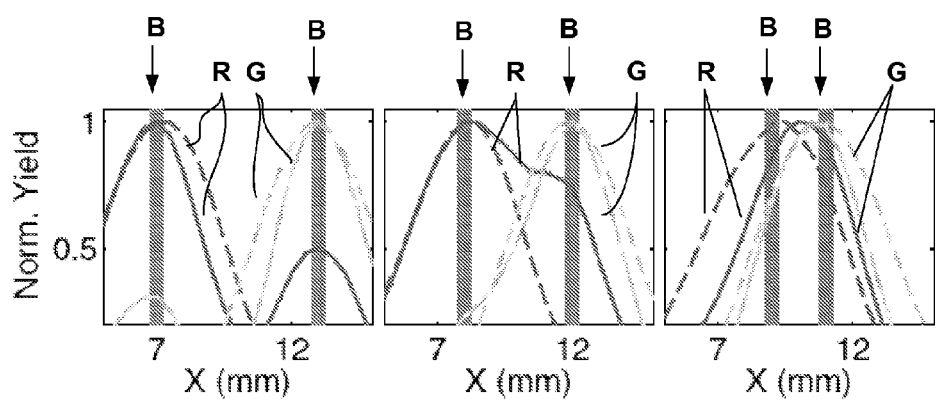
FIG. 2C

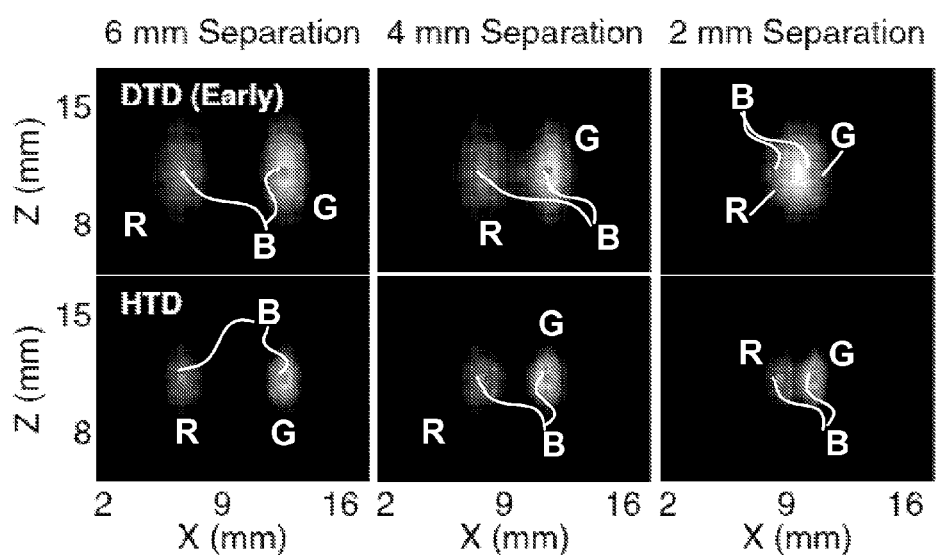
FIG. 3A
FIG. 3B
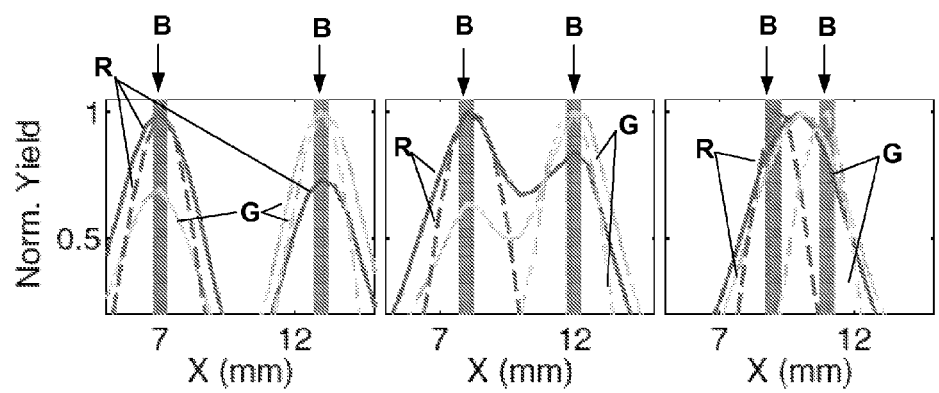
FIG. 3C

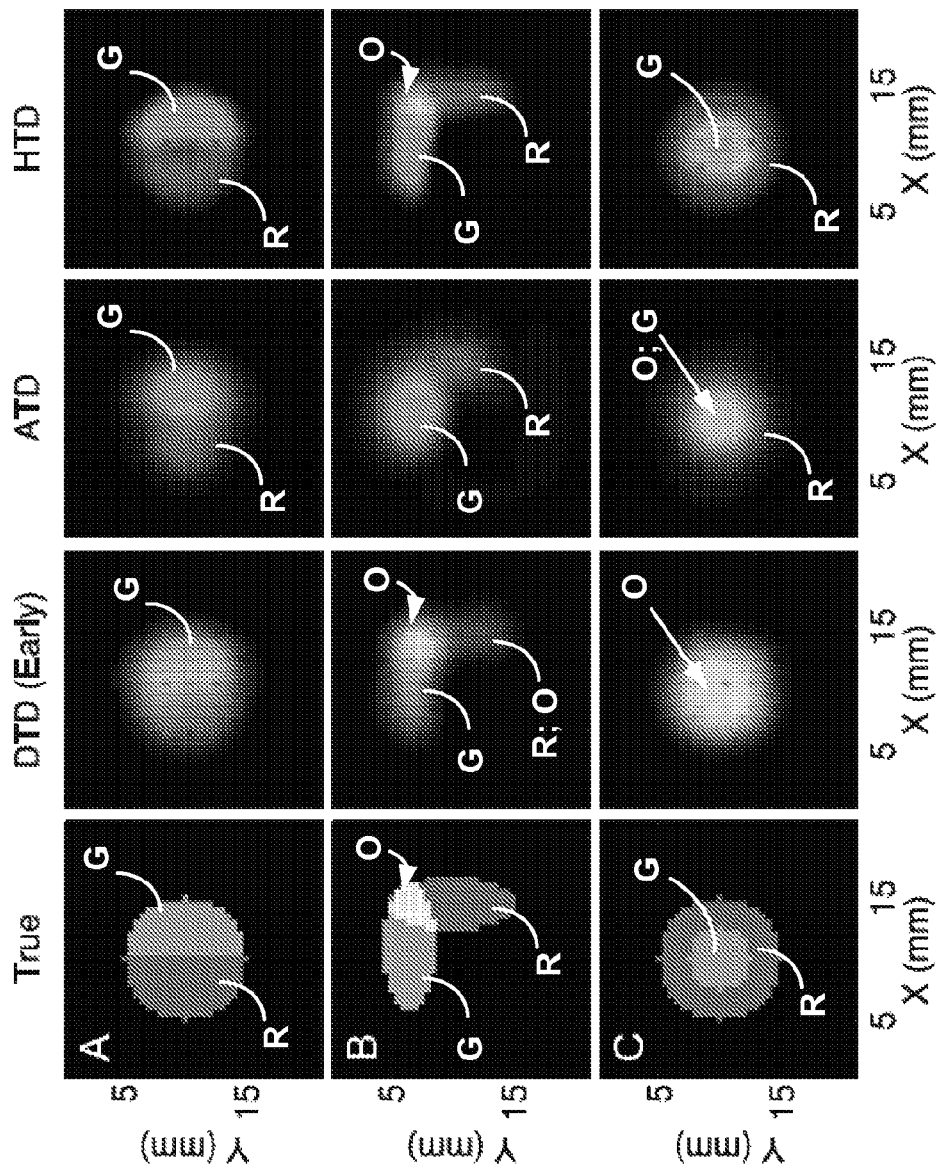

SYSTEM AND METHOD FOR TOMOGRAPHIC LIFETIME MULTIPLEXING

CROSS REFERENCE TO RELATED APPLICATIONS

This application is a 371 application of PCT/US2015/015846 Filed Feb. 13, 2015, which claims priority to U.S. Provisional Patent Application No. 61/939,941, filed on Feb. 14, 2014, the entire contents of which are incorporated by reference herein for all purposes.

STATEMENT REGARDING FEDERALLY SPONSORED RESEARCH OR DEVELOPMENT

This invention was made with government support under Grants Numbers R01 EB015325 and R01 EB000768 awarded by the National Institute of Health. The U.S. government has certain rights in the invention.

TECHNICAL FIELD

The present invention relates to time-domain fluorescent tomography and, in particular, to a method and system optimized for acquisition and analysis of time-domain fluorescent tomographic images that efficiently combine lifetime multiplexing using low cross-talk late-arriving (or asymptotic) photons with the high spatial resolution capability of the early photon tomography.

RELATED ART

Conventional tomography systems utilize continuous-wave (CW) methodology that is incapable to provide the measurement of fluorescence or phosphorescence lifetimes and does not utilize the low-scattering early-arriving photons. While the recently developed time-resolved techniques provide several advantages when used in fluorescence tomography (including lifetime multiplexing and early photon gating, thus allowing for higher resolution), the early time-domain data does not address the problem of poor lifetime sensitivity, resulting in significant lifetime cross-talk and inaccurate localization of closely separated fluorophores with distinct lifetimes.

There remains a need in a fluorescent-tomography-based system addressing these shortcomings of currently used methodologies.

SUMMARY

An embodiment of the present invention provides a method for increasing spatial resolution of optical detection carried out with an optical tomography system Such embodiment includes detecting fluorescent light, emitted by at least one irradiated fluorophore that has been placed inside a turbid medium, to obtain, for at least one source-detector pair of the system and corresponding lifetimes of said at least one irradiated fluorophore a) a first one-dimensional (1D) optical data vector representing fluorescence temporal point spread functions (TPSFs) of said at least one irradiated fluorophore for a first number of early time-windows, and b) a second 1D optical data vector representing decay amplitudes of the at least one fluorophores for a second number of late time-windows. The method further includes forming a third 1D optical data vector by concatenating the first and second 1D optical data vectors and defining a weight matrix that contains (i) time-domain sensitivity functions corresponding to the first one-dimensional optical data vector and (ii) a block diagonal matrix containing continuous-wave sensitivity matrices corresponding to the decay amplitudes. The method further includes identifying a fourth 1D optical vector representing fluorescence yield distribution of the at least one irradiated fluorophore in the turbid medium based on the third 1D optical data vector and the weight matrix. In a specific implementation, the method employs a time-domain fluorescent tomography system.

An embodiment also provides a lifetime time-domain fluorescent tomography system for imaging a turbid sample. Such system includes a pulsed laser source configured to irradiate the sample; an optical system disposed to deliver and collect light, received from the pulsed laser source and re-radiated by the sample. The optical system includes at least one source-detector pair optically cooperated with the sample, wherein an optical detector from the at least one source-detector pair is positioned to detect fluorescent light (emitted by at least one irradiated fluorophore that have been placed inside the turbid sample) for lifetime corresponding to the at least one irradiated fluorophore. The system further includes a programmable processor, operably coupled with tangible non-transitory storage medium and programmed to collect optical data from the optical detector and i) to form a first one-dimensional (1D) optical data vector representing fluorescence temporal point spread functions (TPSFs) of the at least one irradiated fluorophore for a first number of early time-windows, and ii) to form a second 1D optical data vector representing decay amplitudes of said at least one fluorophores for a second number of late time-windows; iii) to form a third 1D optical data vector by concatenating the first and second 1D optical data vectors; and iv) to produce a data output representing fluorescence yield distribution of the at least one irradiated fluorophore in the turbid medium. Such output is formed based at least on the third 1D optical data vector and a weight matrix comprising (j) time-domain sensitivity functions corresponding to the first one-dimensional optical data vector and (jj) a block diagonal matrix containing continuous-wave sensitivity matrices corresponding to the decay amplitudes,

BRIEF DESCRIPTION OF THE DRAWINGS

The invention will be more fully understood by referring to the following Detailed Description in conjunction with the generally not-to-scale Drawings, of which:

FIG. 1A is a plot illustrating fluorescence TSPF for a 2 cm thick diffusive slab with a fluorescent inclusion ($\tau=1$ ns) at the center. The inset shows the full volume at half-maximum (FVHM) of the reconstructed yield for individual time gates.

FIG. 1B shows plots of individual SVD spectra of the DTD weight matrix for one to eight early gates [indicated as I in FIG. 1A]. The gates were stacked in order corresponding to decreasing intensity;

FIG. 1C shows plots of individual SVD spectra of the DTD weight matrix for one to eight late gates [indicated as II in FIG. 1A]. The gates were stacked in order corresponding to decreasing intensity;

FIGS. 2A, 2B, 2C illustrate the results of comparison of reconstructions obtained from applying the ATD and DTD to the same set of 12 late time gates.

FIGS. 3A, 3B, and 3C illustrate the results of comparison of reconstructions obtained from DTD applied to four early gates and those obtained with an embodiment of the method of the invention (HTD).

FIG. 5A: four fluorescent inclusions (those with lifetime $\tau_1$=0.87 ns are marked G, while those with lifetime $\tau_2$=1.27 ns are marked R) are placed in line in the hosting medium. The separation between R1 and R2 is 4 mm, between R2 and G1-2 mm, and between G1 and G2-4 mm. FIG. 5B presents a plot illustrating the results of early-gate reconstruction with the DTD methodology. FIG. 5C illustrates the results of reconstruction with the ATD methodology. FIG. 5D presents the results of reconstruction with an embodiment of the invention.

FIGS. 6A, 6B, and 6C illustrate the results of reconstruction of fluorescent images of objects having complex and overlapping shapes, with the use of the shapes of the "true" objects, those obtained with the early-gate data of the DTD method; those obtained with the ATD method; and those obtained with an embodiment of the invention, HTD method. Objects marked G have lifetimes of $\tau_1$=0.87 ns; objects marked R have lifetimes of $\tau_2$=1.27 ns. Areas marked O indicate areas of image overlap in which objects of both lifetimes are present. The HTD method provides the closest reconstruction to the true shape of the objects.

DETAILED DESCRIPTION

Figures 4A, 4B, 4C, 4D:
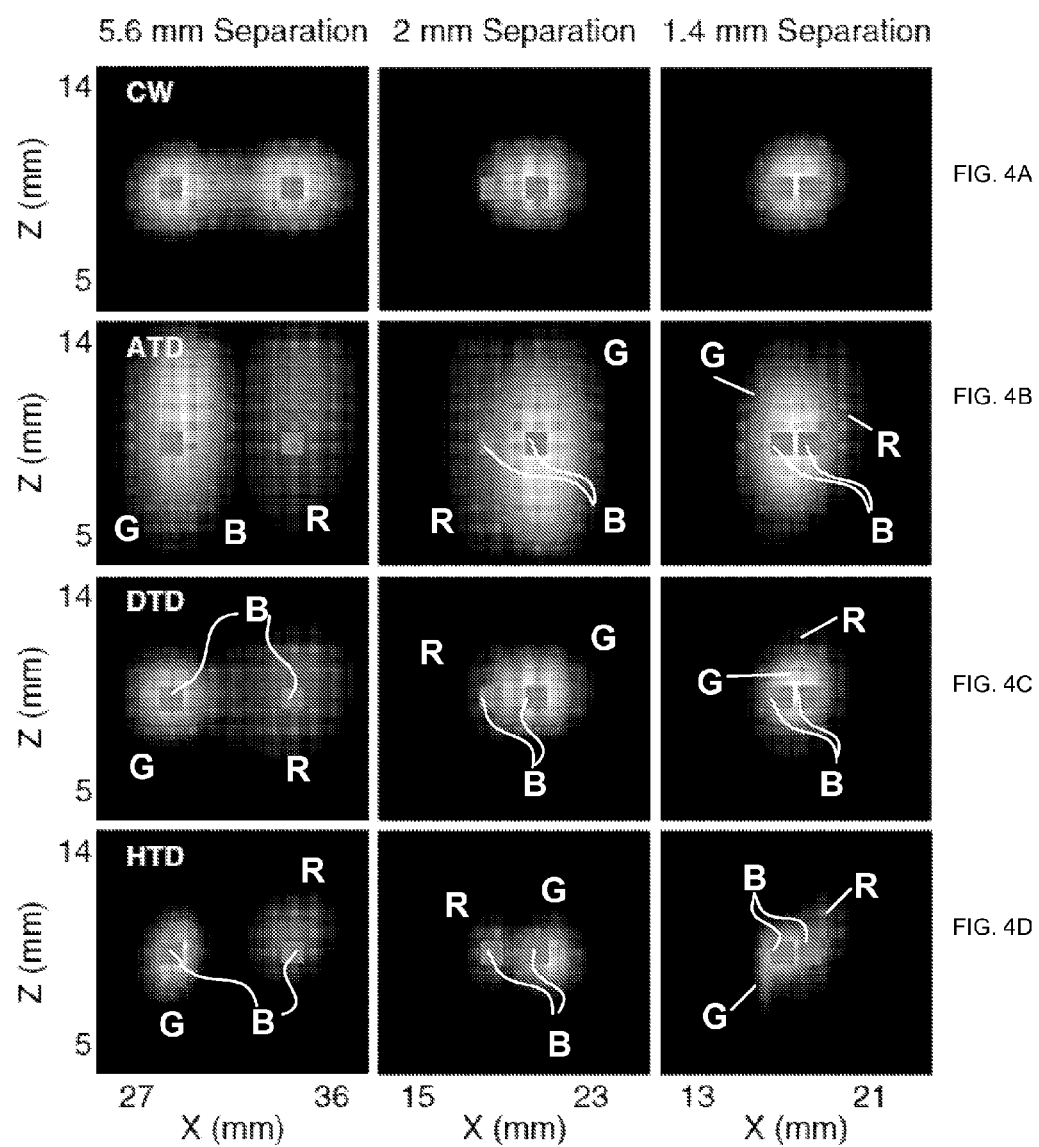
FIGS. 4A, 4B, 4C, 4D, and 4E provide the results of experimental reconstruction of fluorophores with lifetime contrast in a dish phantom obtained with the use of CW, ATD, DTD (three early and three late gates) and the embodiment of the invention with the use of the three early gates.

The idea of the present invention stems from the realization that a late portion of data, representing lifetime of fluorescence of a light-emitting compound affixed to highly-scattering biological tissue, can be expressed through functions that facilitate the separation of the tomography problem into a combination of multiple inverse problems.

The problem of time-domain (TD) tomography in spatially separated imaging targets is solved by employing a methodology of lifetime multiplexing that uses data representing late-arriving (or asymptotic) photons and the high spatial resolution capability of the early-photon tomography. The solution is applied to fluorescence tomography. The spatial resolution demonstrated as a result of employing an embodiment of the invention was shown to be below the point spread function for diffuse optical imaging with minimal cross-talk and distributions narrower than that obtained from either the asymptotic TD (ATD) approach or the direct TD (DTD) approach conventionally used in related art.

Advantages and shortcomings of employing fluorescence-based identification of diseases of or cancer cells in tissue are well recognized. The shortcomings of this methodology include insufficient depth penetration of fluorescent light into the tissue and spatial resolution (of a few millimeters) that is lower than that of the MR-based methods (~50 microns). The advantages include, for example, the ability to track, using diffuse optical imaging, fluorescent markers in a spectral band devoid of water absorption lines and lack of radiation harmful to the tissue. Contrast of fluorescence based imaging is sufficiently high. Fluorescent markers (such as fluorescent proteins) possess power of "intrinsic labeling"/affinity to tumor cells and can provide fluorescence-input that follows tumor growth. Such input, which may not be in some cases sufficiently bright on the background of autofluorescence, nevertheless has different lifetime in comparison with that of autofluorescence. Similarly, the lifetime of fluorescence provide by the markers differ for those markers that are bound to the tissue and those that remain unbound. These properties provide, at least in part, a foundation for distinguishing different targets within the tissue sample using the multiplicity of fluorescent signals received from the tissue simultaneously.

The use of time-resolved techniques in fluorescence tomography using ultrashort pulsed excitation and gated detection have recently gained prominence and provide several advantages, including lifetime multiplexing and early photon gating, thus allowing for higher resolution. In addition to the use of spectrally similar fluorophores, time-resolved imaging enables the separation of fluorophore signals from complex decays arising from tissue autofluorescence.

Time domain methodologies are recognized to provide very comprehensive optical information about a turbid medium, because a short laser pulse used to obtain this information experimentally contains all modulation frequencies including the zero frequency or continuous wave (CW) component. Among the methods for reconstruction of TD data there are direct TD inversion, derived data types such as Laplace transform, Mellin transform or moments, and asymptotic approach based on a multi-exponential analysis.

While the utilization of direct time points from early TD data for data reconstruction can provide higher resolution than CW and late TD data (due to the minimal scattering experienced by early arriving photon), the early TD data offers poor lifetime sensitivity, which results in significant lifetime cross talk and inaccurate localization of closely separated fluorophores with distinct lifetimes (see, for example, Kumar et al., *Opt. Express*, 14, 12255, 2006; hereinafter, Kumar-I).

At the same time, the independently used ATD approach, based on a multi-exponential analysis of the decay portion of the temporal response, is superior to DTD methodology in that it provides superior localization of fluorescence yield distribution in terms of separability of yield distributions for multiple distinct-lifetime fluorophores with low cross talk (see, for example, Kumar et al., *IEEE Trans. Med. Imaging* 27, 1152, 2008; hereinafter, Kumar-II). The strength of the ATD approach is in its ability to completely separate the 3D yield distributions of each lifetime from a mixture of lifetimes present in the imaging medium. The ATD methodology relies on the asymptotic factorization of the TD fluorescence into diffusive and pure exponential fluorescence decay components.

Conventional DTD and ATD Methodologies.

Assuming that the fluorophores under study have lifetimes $\tau_n$ that are longer than the intrinsic diffusion time scale $\tau_D$ (a condition widely satisfied for biological tissue, see Kumar I), the TD fluorescence signal asymptotically approaches a multi-exponential sum, with decay amplitudes each of which is linearly related to a yield distribution $\eta_n(r)$ of the particular lifetime $\tau_n$. The fluorescence temporal point spread function (TPSF) for impulsive excitation at source position $r_s$ and detection at $r_d$ on the surface of a bounded transport medium of support $\Omega$ takes the form:

$$U_f(r_s,r_d,t)=\Sigma_{n=1}^N\int_\Omega W_n(r_s,r_d,r,t)\eta_n(r)d^3r \quad (1)$$

where $W_n=G^X(r_s,r_d,t)\otimes \exp(-t/\tau_n)\otimes G^m(r_s,r_d,t)$ is the TD sensitivity function, expressed as a double convolution of the source and detector's Green functions, $G^X$ and $G^m$, for light transport in the medium and a fluorescence decay term.

The DTD approach results from the direct inversion of the equation $$y=W\eta \quad (2)$$

which, in turn, results from the re-writing of Eq. (1) as a linear matrix equation (for M source-detector pairs, L time gates, and N lifetime-components) by discretizing the medium volume into V voxels. In Eq. (2), y is a (ML×1) vector of the measured fluorescence data $U_f$; $W=[W_1, \ldots W_N]$ is a (ML×VN) matrix of TD sensitivity functions, and $\eta=[\eta_1,\eta_2, \ldots \eta_N]^T$ is a (VN×1) vector of fluorescence yield distributions for all lifetimes.

The inverse problem is expressed in a standard way using the Tikhonov regularization (see *Introduction to Inverse Problems in Imaging*, Bristol: IOP Publishing, 1998) to recover $\eta$, which in the DTD approach is given by $$\eta^{DTD}=W^T(WW^T+\lambda I)^{-1}y \quad (3)$$

The ATD approach results from recasting the TD forward problem in an alternate form in the asymptotic limit (i.e., for times much longer than the intrinsic diffusion timescale $\tau_D$ of the medium). The $W_n(t)$ in Eq. (1) can then be factored into a product of CW sensitivity functions and simple exponential decays for arbitrary transport media, and Eq. (2) can be expressed, for $t\gg\tau_D$, as $$y=A\overline{W}\eta \quad (4)$$

where $A=[\exp(-t/\tau_1)*I, \ldots, \exp(-t/\tau_N)*I]$ is a (ML×MN) basis matrix of exponential decays, I is an (M×M) identity matrix, and
$\overline{W}=diag(\overline{W}_n)$ is a (MN×VN) block diagonal matrix containing CW weight matrices, $\overline{W}_n$, which are evaluated with the background absorption reduced by $1/v\tau_n$ (see Kumar I; see also Kumar et al., *Opt. Lett.*, 30, 3347, 2005; hereinafter, Kumar-III).

The Eq. (4) allows an approach to solving the TD inverse problem in the asymptotic limit. Since A is a well-conditioned matrix, it can be first inverted without regularization by multiplication with its Moore-Penrose pseudoinverse $A^+$. At the same time, $A^+y$ is simply a linear least-squares solution for a multiexponential analysis of the raw time resolved data (y): $A^+y=a$, where $a=[a_1, \ldots, a_N]^T$ is a (MN×1) vector of decay amplitudes for all source-detector pairs and lifetimes. Applying Tikhonov regularization to invert the decay amplitudes ($A^+y$), a matrix representation of the all-lifetime fluorescence yield in the ATD approach can be expressed as:

$$\eta^{ATD}=\overline{W}^T(\overline{W}\overline{W}^T+\lambda I)^{-1}A^+y \quad (5)$$

Although the forward problems of DTD, Eq. (2), and ATD, Eq. (4), are equivalent for late time gates, the corresponding inverse problems (Eqs. (3) and (5)) are distinct and will produce different reconstructions even when applied to the same measurement. The key aspect of the ATD approach is that the basis matrix A is removed from the regularization step. This ensures that the measurements in y are directly separated using the exponential basis function of each fluorophore. Additionally, given the block diagonal nature of $\overline{W}$, Eq. (5) essentially reduces to completely separate inverse problems for each yield distribution $\eta_n$. This should be contrasted with the DTD inversion in Eq. (3), where the inverse problem for each $\eta_n$ is not separable. Consequently, the ATD approach results in significantly lower cross talk between the yields of multiple lifetimes than the DTD approach, and at the same time suffers from poorer lifetime separation. Although the DTD approach is suboptimal for lifetime multiplexing, the early and peak portions of the TD signal provide higher resolution and better noise statistics than the late photons (see Niedre et al, *Proc. Natl. Acad. Sci. USA* 105, 19126, 2008).

The present invention stems from the realization that, at least for the purposes of lifetime multiplexing in TD fluorescence tomography, a single inverse problem can be defined, which combines the resolution capability of the early portion of time-domain data with the lifetime multiplexing capability of the later portion, and solved using Tikhonov regularization that accounts for the distinct noise characteristics of the early and late time-domain data.

Figure 10:
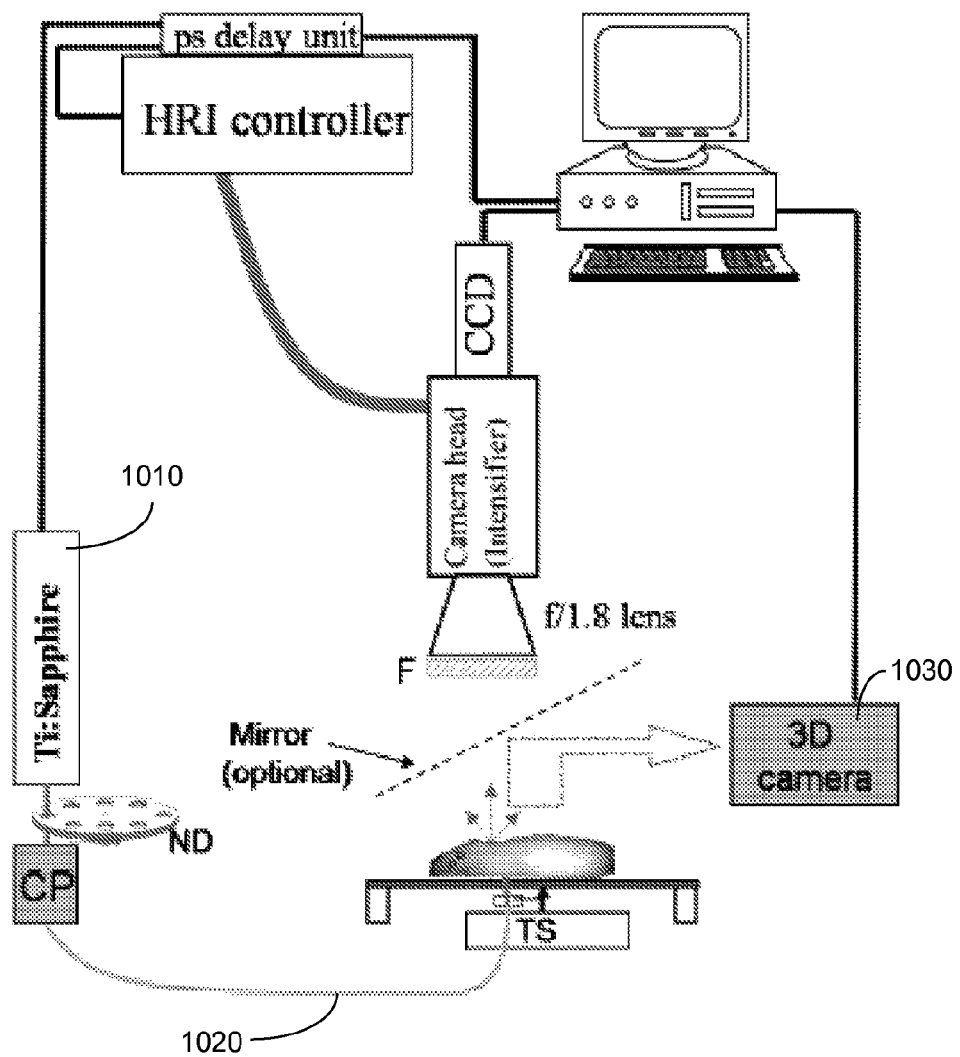
FIG. 10 schematically illustrates an optical system according to an embodiment of the invention.

According to an embodiment of the invention (referred to as the HTD approach), and in reference to FIG. 10, fluorescence was excited with the pulsed broadband (from about 480 to about 950 nm) output of a titanium-sapphire-laser 1010 (800 nm@80-MHz repletion rate, Spectraphysics, Santa Clara, Calif.) driven photonic crystal fiber 1020 (Thorlabs NL-PM-750, Newton, N.J.) filtered through either 495+/−25 nm or 543+/−5 nm optical pass-band filter (not shown). The resulting fluorescence emission was detected with either a 529+/−25 nm filter, or a 560-nm long pass filter coupled to an intensified CCD camera 1030 (PicostarHR, LAVision, Gmbh; 500-ps gate width, 600-V gain, 150-ps steps, 4×4 hardware binning) The levels of excitation powers were ~50 µW/cm² at both 495 and 543 nm. Camera integration times ranged from 100 ms to 3 s. In a specific embodiment, the optical signals can be detected with the use of wide-angle detection (using, for example, gated intensified CCD/ICCD cameras). It is appreciated that in a related embodiment the optical data can be collected in reflection from the sample. It is also appreciated that the excitation and emission filters, used with the photonic crystal fiber output as disclosed above, are not necessarily used in every embodiment. For example, the output from the Ti-sapphire laser can be used with different emission filters (such as an 800 nm long pass filter for the experiments disclosed in reference to FIG. 4 below.)

The so-acquired time-resolved data includes a signal from the earliest arriving photons that have travelled through the biological sample with minimal scattering, and late arriving photons that mostly correspond to the fluorescence lifetime decay.

According to an algorithm of the invention, based on the acquired time-resolved data a first data set Y is formed that includes both the early time gates and the decay amplitudes:

$$Y=[y(t_1),y(t_2), \ldots, a_1, a_2, \ldots]^T \quad (6)$$

This data set is then inverted by a weight matrix $W_H$ that includes both the weight function $W$ of the DTD and the weight function $\overline{W}$ of the ATD. Then, according to an idea of the invention, the forward problem takes the form $Y=W_H \eta$ or, explicitly, $$\begin{bmatrix} y(t_1) \\ y(t_2) \\ \vdots \\ a_1 \\ \vdots \\ a_N \end{bmatrix} = \begin{bmatrix} W_1(t_1) & \cdots & W_N(t_1) \\ W_1(t_2) & \cdots & W_N(t_N) \\ \vdots & \cdots & \vdots \\ \overline{W}_1 & 0 & 0 \\ 0 & \ddots & 0 \\ 0 & 0 & \overline{W}_N \end{bmatrix} \begin{bmatrix} \eta_1 \\ \vdots \\ \eta_N \end{bmatrix} \quad (7)$$

With the imposition of a positivity constraint on the Tikhonov cost functional, the inversion of the HTD approach is expressed as the minimization problem:

$$\eta^{HTD} = \arg\min_{\eta \geq 0} \|Y - W_H \eta\|^2_{C^{-1}} + \lambda \|\eta\|^2 \quad (8)$$

where C is a measurement covariance matrix that incorporates the distinct noise characteristics of the direct time points y and the amplitudes a within Y. The positive constraint reduces cross-talk in the approach of the invention by preventing negative yield values from spuriously reducing the ATD term ($\overline{W}_n$) of the HTD cost function on Eq. (8). As can be seen from Eqs. (7) and (8), the method of reconstructing the fluorescence yield obtained with the use of the HTD approach provides both (i) high resolution and improved noise statistics for the early (early-gate) and peak portions of the TD signal and (ii) low cross-talk and good tomography localization of multiple fluorophores with distinct lifetimes for the asymptotic (late-gate) portion of the TD signal.

Identification of Asymptotic Regime (ATD Condition)

For lifetime $\tau_n$, the time-domain weight function can be re-written in terms of the background weight function $W_B$ $$W_B(r_s,r_d,r,t) = \int_0^t dt'' G^x(r_s,r,t'-t'') G^m(r,r_d,t'') \quad (9)$$

(where $G^x$, $G^m$ represent Green functions of radiation transport equation) and an exponential decay function:

$$W(r_s,r_d,r,t) = \int_0^t dt' W_B(r_s,r_d,r,t') \exp(-(t-t')/\tau_n) \quad (10)$$

$$W(r_s,r_d,r,t) = \exp(-t/\tau_n) f(t) \quad (11)$$

Where f(t) is defined as:

$$f(t) = \int_0^t dt' W_B(r_S,r_d,r,t') \exp(-t'/\tau_n) \quad (12)$$

To approximately identify the asymptotic regime (corresponding, generally, to late time-gates in the experimental acquisition of optical data), the start of the asymptotic regime can be denoted as $t=t_{ATD}$. The value of $t_{ATD}$ can be defined, for example, as a moment of time for which $f(t_{ATD})=0.99 f(\infty)$. Notably, since $W_B$ decays in proportion to $t \cdot \exp(-t/\tau_D)$, the value of $t_{ATD}$ in practice depends on an effective time constant, $\tau_{eff} = (1/\tau_D - 1\tau_n)^{-1}$, which in turn also depends on both the diffusion time constant of light transporting the background turbid medium, $\tau_D$, and the intrinsic fluorescence lifetime, $\tau_n$.

Verification of Operation of Embodiment.

To quantify the proposed approach in comparison with the DTD and ATD methodologies of the related art, the Monte Carlo simulations were applied to the model described by a 2×2×2 cm³ slab of the turbid medium and characterized by optical parameters $\mu_a=0.2$ cm$^{-1}$ and $\mu'_s=10$ cm$^{-1}$ where $\mu_a$, is the absorption coefficient (probability of photon absorption per unit infinitesimal length) and $\mu'_s$ is the reduced scattering coefficient (the probability of a photon direction becoming random due to scattering per unit infinitesimal length) The sources-detectors pairs were represented by forty-nine source and forty-nine detectors equally spaced at the opposite facets of the slab (planes z=0 and z=2 cm, respectively. The time step (i.e., the temporal separation between subsequent measurements) was set to 100 ps. The fluorophore particles of 0.125 mm³ in volume were assumed to be included at the center of the slab. A 2% shot noise was added to all forward data prior to reconstruction. Minimization of the cost functional of the HTD embodiment of the inventions with positivity constraint was implemented using L-BFGS-B (discussed by Byrd et al., *SIAM J. Sci. Comput.*, 16, 1190, 1995) in MATLAB (The Mathworks, Inc.). In all simulations, the regularization parameter λ was chosen to correspond to the least-mean-square error, MSE, such that $MSE = \|\eta_{recon} - \eta_{true}\|$.

Generally, the time-step value represents the time-delay between the laser pulse at t=0 ps and the moment the data is taken in a given time-gate. For example, at t=0 ps, the time-gate is open for 500 ps; then at t=100 ps, the time-gate is open for 500 ps; at t=200 ps, the time-gate is open again for 500 ps, etc. The duration of a time-step can be shorter than that of the time-gate.)

FIGS. 1A, 1B, 1C illustrates the results of simulation of the fluorescence yield with the use of the DTD approach of the related art for a single fluorescent inclusion (single fluorophore element, τ=1 ns). Here, the time-dependence of the TSPF is divided into a portion I corresponding to the early time-gates and a portion II corresponding to the late time-gates. The inset of FIG. 1A, illustrating the full volume at half-maximum (FVHM) of the yield reconstructed according to Eq. (3), for individual time-gates, shows that the resolution quantified by the FVHM value decreases with time (i.e., for late time-gates). A singular-value decomposition (SVD) analysis of the DTD sensitivity matrix shows distinct behavior for the early and late portions of the TPSF. The SVD spectra of the DTD weight matrix are shown in FIG. 1B for one to eight early time-gates (corresponding to the portion I of FIG. 1A) and in FIG. 1C for one to eight late time-gates (corresponding to the portion II of FIG. 1A). Specifically, as shown in FIG. 1B, the slope of the singular value spectra increased with the number of early time gates, indicating improvement in the conditioning of the inversion and gains in resolution. At the same time, the SVD spectra show negligible change for any combination of multiple late time gates, as follows from FIG. 1C. This demonstrates the redundancy of using multiple gates in the asymptotic (late in time) region for tomography, as can be expected from the spatio-temporal factorization in Eq. (4).

The comparison of the imaging performance with the use of the DTD and ATD approaches with the methodology of the present invention was carried out with the use of two fluorophores in the above-defined model, each of which fluorophores had a distinct lifetime ($\tau_1=0.87$ ns and $\tau_2=1.27$ ns, respectively); the spatial separation between the locations of such fluorophores was varied between 2 and 6 mm. In reference to FIGS. 2A-2C and 3A-3C discussed below:

Data-distributions marked R and G correspond to the yield-distributions for 0.87 and 1.27 ns, respectively.

The true locations of the fluorescent inclusions are shown with bands B.

The X-Z plots were generated by assigning the recovered yields to the red (0.87 ns) and green (1.27 ns) components of the RGB colormap.

Each data-distribution is thresholded at 50% of its maximum.

Example 1

FIGS. 2A, 2B, 2C illustrate a comparison between the reconstructed fluorescent images procured with the use of the ATD and DTD methodologies that were applied to the same set of 12 late time-gates. The three X-Z plots of each of FIGS. 3A, 3B correspond, respectively, to fluorophore-to-fluorophore separation of 6 mm, 4 mm, and 2 mm along the x-axis. FIG. 2C provides line plots for ATD (dashed line) and DTD (solid line) along the x-axis at the depth of the inclusion, obtained from the data of FIGS. 2A, 2B. The computation time for ATD was 21 times shorter than that for DTD. It can be seen from the line plots of FIG. 2C that there is significantly higher cross-talk for reconstructions obtained with the use of the DTD than that in case of the ATD reconstruction. Such high-level of cross-talk in practice precludes accurate localization of the fluorophores with the use of the DTD method even for a 4 mm separation. The ATD approach, however, provides minimal cross-talk and facilitates a process of correct localization of the fluorescent inclusions in the turbid medium of the model, down to the 2 mm separation between the locations of the inclusions.

Example 2

FIGS. 3A, 3B, 3C show the comparison of the results of yield reconstructions obtained with the use of the using the DTD approach with four early time-gates and those obtained with the embodiment of the invention according to Eqs. (7), (8). Each of FIGS. 3A and 3B includes three X-Z plots corresponding, respectively, to separations of 6 mm, 4 mm, and 2 mm along the x-axis. FIG. 3C provides line plots for fluorescent yield distribution obtained—with the HTD embodiment of the invention (dashed line) and DTD (solid line) along the x-axis at the depth of the inclusion—from the data of FIGS. 3A, 3B.

From the early DTD data it can be observed that, while the individual yield distributions are smaller than the ATD-derived distributions of FIG. 2B, the cross-talk is significantly higher than that characterizing the ATD distributions for all separations. Therefore, localization of the fluorophores in reliance on the early DTD data only once again leads to inaccurate results. For comparison, the yield reconstruction performed with the proposed HTD approach utilizing four early time-gates and the decay amplitudes (dashed lines) demonstrates high resolution and accurate localization for all fluorophore-to-fluorophore separations. Is notable that, when the positivity constraint of Eq. (8) was not imposed, the cross-talk in spatial localization of the fluorophores with the embodiment of the invention was higher, but still lower than for that of the DTD alone.

Example 3

Additional independent validation of advantageous performance of the embodiment of the invention, phantom experiments were performed. To this end, parallel tubes filled with two dyes ($\tau_1$=0.87 ns and $\tau_2$=1.27 ns, respectively) and separated by 5.6, 2, and 1.4 mm, in three different scenarios, were embedded in a scattering medium consisting of intralipid and nigrosin ($\mu_a$=0.1 cm$^1$ and $\mu^0_s$=10 cm$^1$). Measurements were performed with a TD fluorescence tomography system that included a Ti-Sapphire laser for excitation and time-gated intensified CCD camera for detection. Full tomographic measurements were acquired for up to 84 sources and 84 detectors, and 46 time gates, with a time-gate width of 500 ps, CCD integration time of 100-200 ms, and the time-step size of 150 ps. The experimental reconstruction of fluorophores with life-time contrast in such phantom are illustrated in FIGS. 4A, 4B, 4C, 4D, and 4E.

Here, data-distributions marked R and G correspond to the yield-distributions for 0.87 and 1.27 ns, respectively; the true locations of the fluorescent inclusions are shown with bands B; the X-Z plots were generated by assigning the recovered yields to the red (0.87 ns) and green (1.27 ns) components of the RGB colormap; and each data-distribution was thresholded at 70% of its maximum.

Figure 4E:
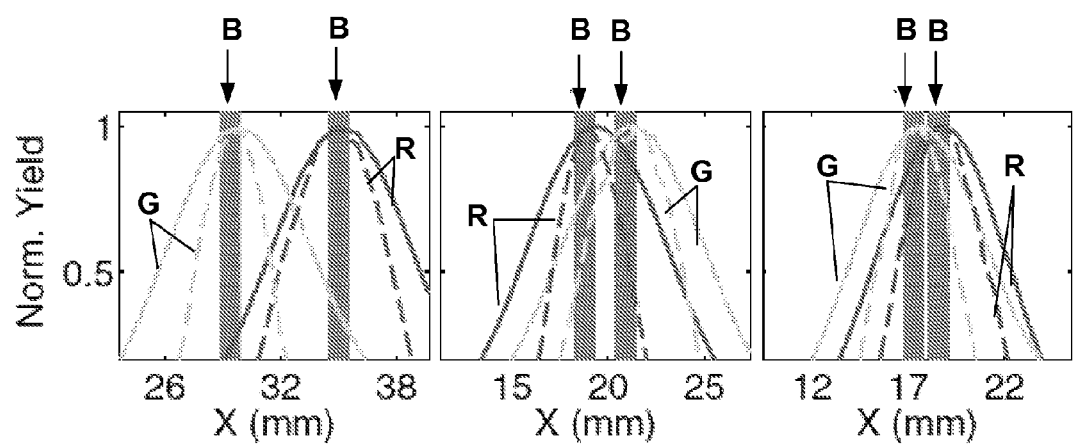

FIGS. 4A, 4B, 4C, and 4D present the X-Z plots of data distribution obtained with the use of CW, ATD, DTD (three early and three late gates), and the embodiment of the invention (HTD) combining the ATD and DTD (three early gates). Each of FIGS. 4A, 4B, 4C, ad 4D includes three X-Z plots corresponding, respectively, to separations of 5.6 mm, 4 mm, and 1.4 mm along the x-axis. The markings and other associated data are the same as in FIGS. 2A, 2B, 2C. For example, data-distributions marked R and G correspond to the yield-distributions for 0.87 and 1.27 ns lifetimes, respectively. The true locations of the inclusions are shown with bands B. Each distribution is thresholded at 70% of its maximum. For comparison, FIG. 4E provides line plots for the results obtained with the embodiment of the invention (dashed line) and those for ATD (solid line) along the x axis at the depth of the inclusion, obtained from the FIGS. 4B and 4D.

It is easily discerned that the fluorescent yield reconstruction performed with the use of the ATD methodology facilitates correct localization of the tubes for all spatial separation values, while the capabilities of the DTD and CW approaches fall short at separation smaller than (in this case) 5.6 mm. In contradistinction, the use of the method of an embodiment of the invention applied to three early time gates and decay amplitudes not only provides accurate localization of the fluorescent inclusions but also significantly narrower yield distributions as compared to those resulting from the application of the ATD methodology. Notably, since the same regularization was applied for the ATD-based reconstruction (the results of which are shown in FIG. 4E) as in the HTD method of the invention (see also FIG. 4E), the improvement in spatial resolution is attributed to the incorporation of early time-gates in the HTD-based reconstruction.

It is appreciated, therefore, that embodiments of the invention are structured, on the one hand, to gain high spatial-resolution advantage provided by processing both early and late time-gate fluorescent tomographic data with the use of a matrix including both time-domain sensitivity functions and CW weight matrices evaluated with the reduced background absorption. The proposed approach for TD fluorescence tomography combines the use of early- and late-arriving photons, enabling high-resolution lifetime tomography in turbid media. In contradistinction with the proposed methodology that results in increase of the resolution and precision of localization of fluorescent lifetime tomography, the use of direct inversion of late time-gate optical data can lead to erroneous localization and is computationally more cumbersome than an asymptotic approach of the related art that utilizes only the decay amplitudes. The experimentally proven increase in resolution and cross-talk performance of the proposed method in separating closely located targets can be further advanced in practice by using faster detectors that are capable of detecting photons arriving earlier than, for example, 100 ps.

Related Embodiment of the Invention

A unique feature of the time-domain weight matrix W in the asymptotic regime (corresponding to late time-gates) is that the decay profile for each lifetime component is independent of voxel location. The total time-domain measurement data for these time points can be readily separated into temporal terms which correspond to each lifetime. On the other hand, this time-domain weight matrix W for early time-gates contains different temporal profiles at each voxel. For a time-domain measurement at these early time-gates, it is no longer possible to determine the temporal terms that correspond to each lifetime component without considering the spatial distribution of the fluorophores.

For the early time gates, instead of attempting to separate different fluorophores using the time-domain measurement data, it is possible to consider separation of the fluorophores at the voxel level using the results of fluorescent yield reconstructions derived from late time-gates. In one implementation, such separation is effectuated in a form of a spatial prior, by incorporating of a low-resolution estimate of an object being imaged as prior information in the optical reconstruction process. In particular, an initial estimate of the yield is obtained for lower resolution but well separated fluorescent signals with the use of the ATD approach as applied to late time-gates ($\eta^{ATD}$). Next, reconstruction on early time-gates is performed with the spatial regularization matrix $$L = \text{diag}(1/\eta^{ATD}) \quad (13)$$

encoded with the ATD reconstruction to obtain, for the fluorescent yield acquired with an embodiment of the invention, $$\eta^{HTD} = (W^T W + \lambda L^T L)^{-1} W^T y \quad (14)$$

Empirical Results.

Figures 5A, 5B, 5C, 5D:
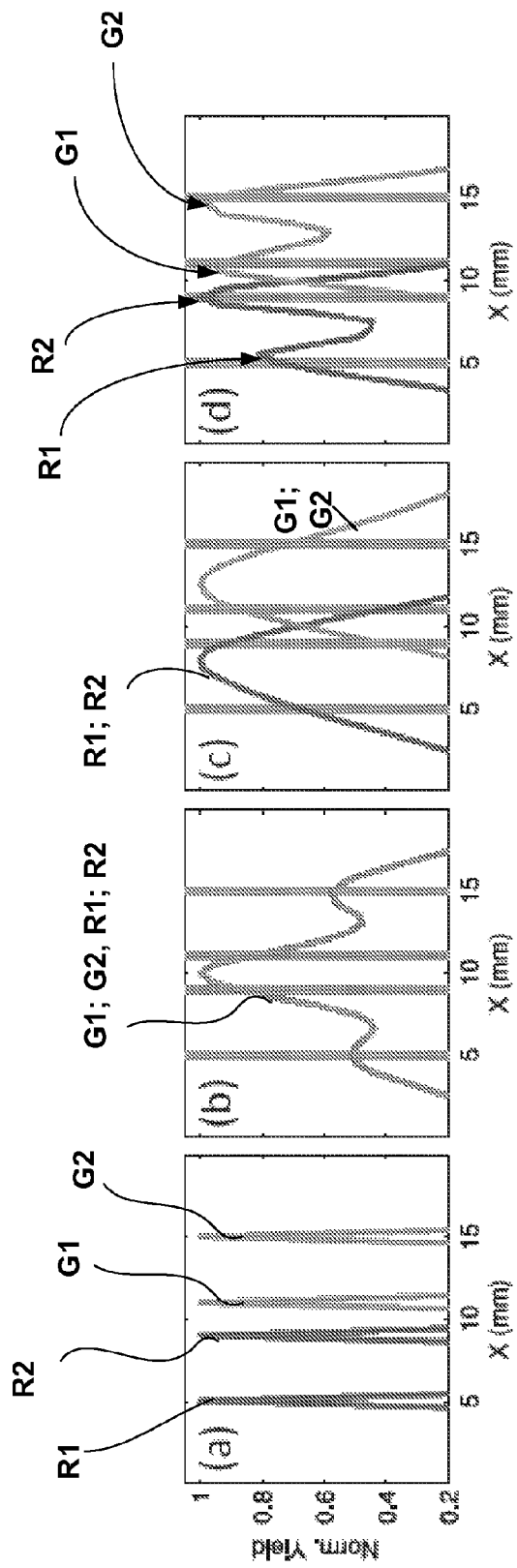
FIGS. 5A, 5B, 5C, and 5D illustrate the application of an embodiment of the invention to resolving loosely-spaced fluorescent objects having different lifetimes.

Various experiments have been performed to demonstrate the advantages of the method of the invention in spatially resolving fluorophores having different lifetimes. FIGS. 5A, 5B, 5C, and 5D, for example, illustrate the application of an embodiment of the invention to resolving loosely-spaced fluorescent objects having different lifetimes. FIG. 5A shows fluorescent yield distributions representing four fluorescent inclusions (those with lifetime $\tau_1=0.87$ ns are marked G, while those with lifetime $\tau_2=1.27$ ns are marked R), which are placed in line in the hosting medium. The separation between the R1 and R2 fluorophores is about 4 mm, between R2 and G1 fluorophores—2 mm, and between G1 and G2 fluorophores—4 mm. The optical data reconstruction performed with the use of early time-gate data and the DTD methodology is shown in FIG. 5B, while the images reconstructed with the use of the ATD method are shown in FIG. 5C. The early-gate DTD clearly does not allow for resolving of not only between the spatially-separated elements of the same lifetime, but even between the longer lifetime elements from the shorter-lifetime elements. The ATD clearly differentiates between the shorter-lifetime elements and the longer-lifetime elements (R1, R2 and G1, G2) but is it still deficient with respect to identifying individual components having the same lifetime and separated spatially. In contradistinction, the proposed methodology demonstrates, in FIG. 5D) a convincingly higher spatial resolution, resolving four peaks corresponding to individual fluorophores G1, G2, R1, R2 present in the object (as shown in FIG. 5A).

FIGS. 6A, 6B, and 6C illustrate the results of a related simulation. Here, fluorescent images of objects having complex and overlapping, on the background of the hosting medium, shapes are being reconstructed. Each of FIGS. 6A, 6B, 6C contains three images: one corresponding to the ideally resolved object ("true" image), another representing the reconstruction of the overlapping objects with the use of early time-gate data and the DTD method; that obtained with the ATD method; and that obtained with an embodiment of the invention, HTD method. The three examples of visually overlapping objects are: a) adjacent semi-circles in FIG. 6A; b) overlapping ellipses in FIG. 6B; and c) concentric circles in FIG. 6C. In practice, these objects can be located in different object planes (i.e., one of them is closer to the optical detector than another and partially screens the other object. Objects marked G have lifetimes of $\tau_1=0.87$ ns; objects marked R have lifetimes of $\tau_2=1.27$ ns. In all test cases, objects with a thickness of 5 mm are embedded in the center of a 2 cm thick slab of hosting material.

In portions of FIGS. 6A, 6B, and 6C representing the results of image reconstruction, areas marked O indicate areas of image overlap. In particular, the separation capabilities of the early time-gate DTD are the least pronounced, demonstrating, for example, a practical lack of differentiating and/or distinguishing the two concentric circles presenting, instead, a blurred image field of "overlap") occupying most of the image field and surrounded by a narrow, poorly defined annulus of R-object. The separation capability of the ATD-image of FIG. 6C, on the other hand, is higher: here, the R and G objects can be somewhat resolved. The degree of spatial resolution provided by the method of the invention, however, is superior to both methods of the related art, as FIG. 6C clearly demonstrates. A skilled artisan will unambiguously come to the similar conclusion based on the convincing demonstrations of FIGS. 6A and 6B.

Figures 7A, 7B, 7C, 7D, 7E:
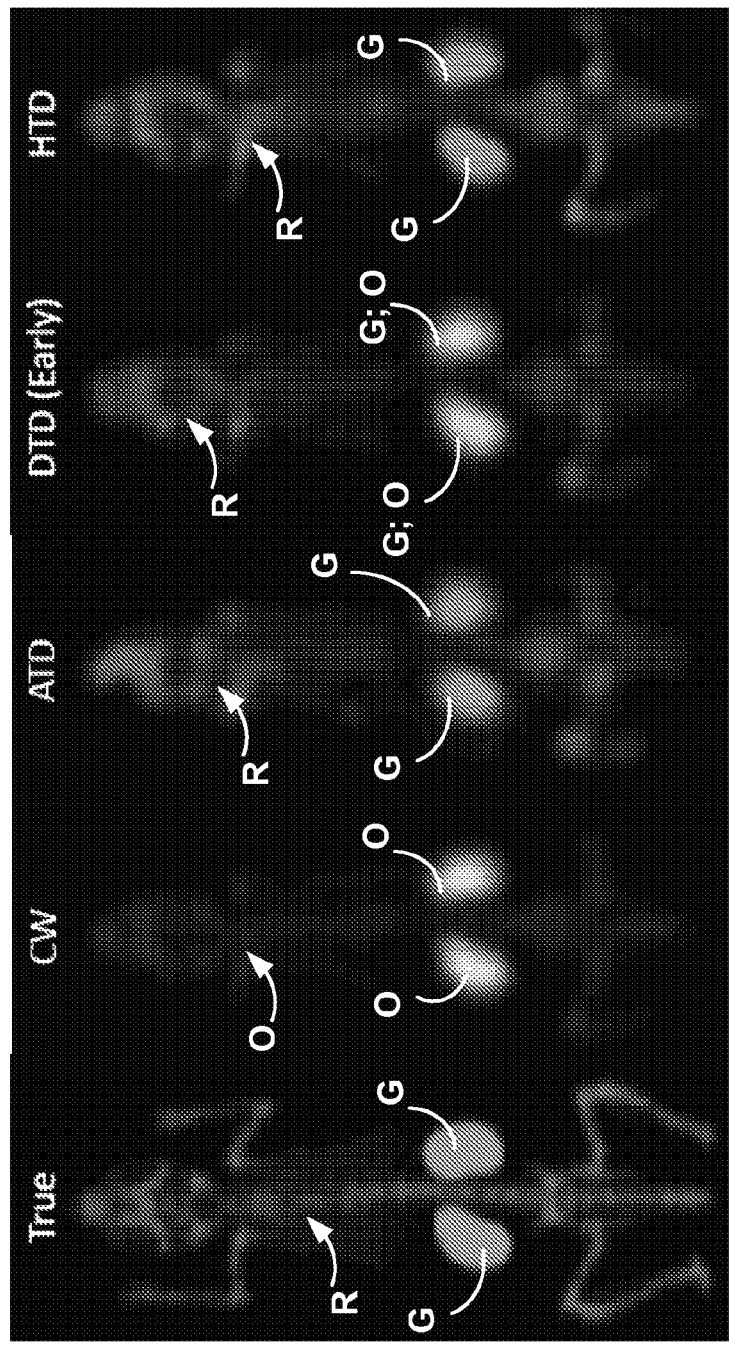
FIGS. 7A, 7B, 7C, 7D, and 7E are images representing tomographic lifetime multiplexing of organ-targeted fluorophores, using the Digimouse atlas with 84 sources and 84 detectors (84 source-detector pairs). The lifetimes of the skeleton and kidneys (marked in "true" image with R and G, respectively) were $\tau_s$=0.5 ns and $\tau_k$=0.85 ns. Presented are the results of reconstruction with CW methodology (FIG. 7B); the ATD methodology (FIG. 7C); early time-gate data of the DTD method (FIG. 7D); and the method of the invention (FIG. 7E). Areas marked O indicate areas of image overlap in which objects of both lifetimes are present.

In a related experiment, tomographic lifetime multiplexing of organ-targeted fluorophores was performed using the Digimouse atlas with 84 sources and 84 detectors (84 source-detector pairs). Time-gate width was chosen to be 500 ps. The lifetimes of the skeleton and kidneys (marked in a "true" image of FIG. 7A with R and G, respectively) were $\tau_s=0.5$ ns and $\tau_k=0.85$ ns. FIGS. 7B, 7C, 7D, and 7E are images representing the results of reconstruction with CW methodology (FIG. 7B); the ATD methodology (FIG. 7C); early time-gate data of the DTD method (FIG. 7D); and the method of the invention (FIG. 7E). Areas marked O indicate areas of image overlap in which the different objects are not necessarily well resolved. It is quite apparent, just as it was in the case of FIGS. 6A-6C, that the separation capability of the ATD method is superior to that of the early-gate DTD method, conventionally used in related art; and that the spatial resolution capability of the HTD method of the invention is superior to that of the ATD method.

Figure 8:
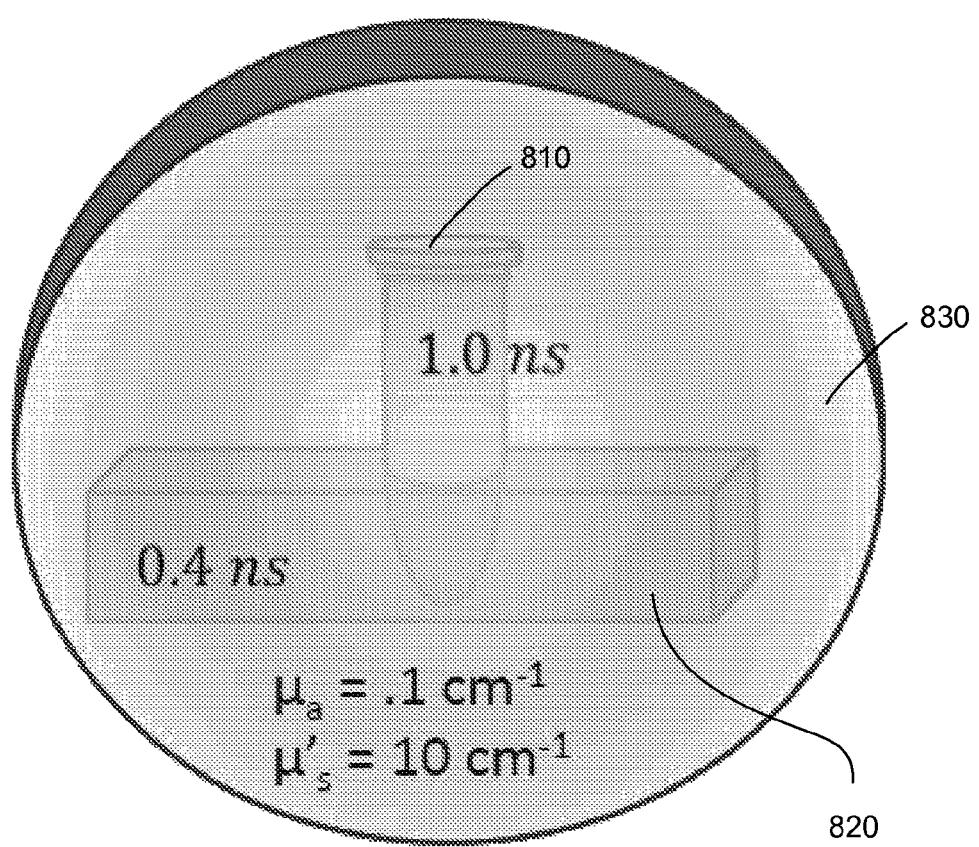
FIG. 8 provides a schematic diagram of an embedded fluorophore phantom; with an example of a tube (containing medium with a lifetime of $\tau_2$=1.0 ns embedded inside a host medium with a lifetime of $\tau_1$=0.4 n). Both objects are shown submerged in an 88-mm-diameter culture dish.
Figures 9A, 9B:
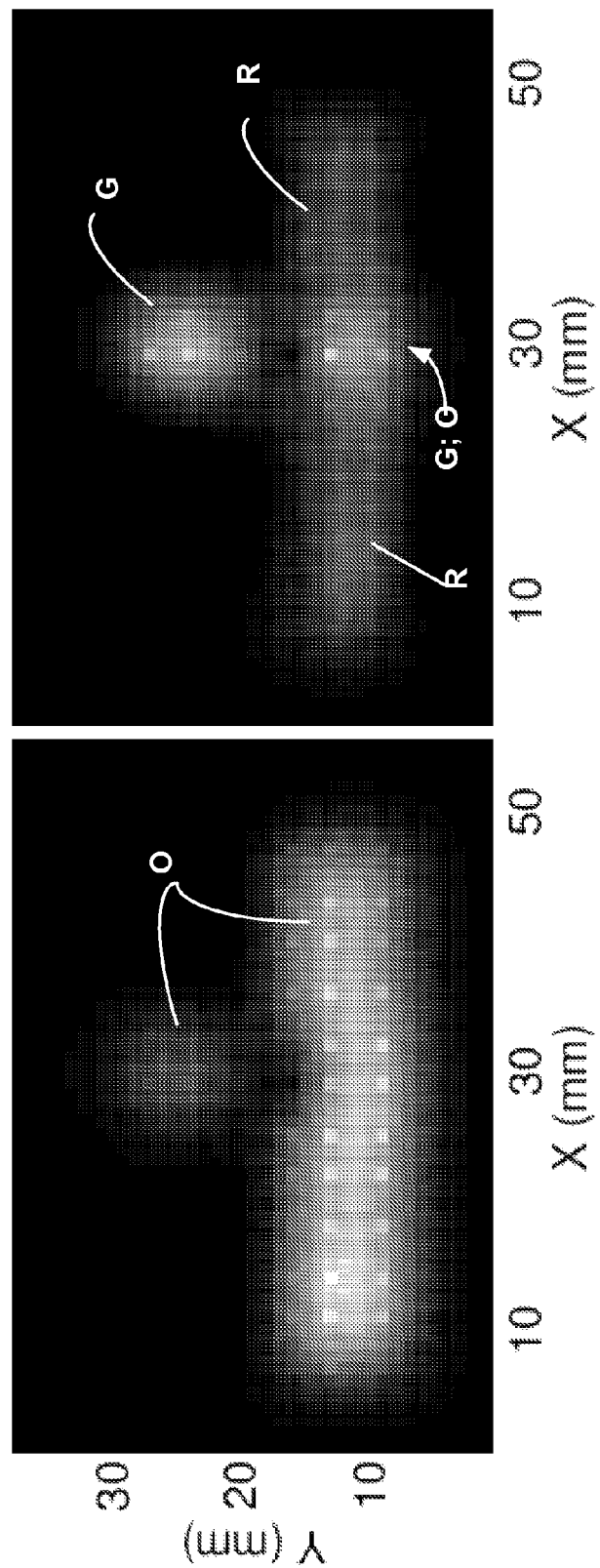
FIGS. 9A and 9B provide the results of reconstructions for the embedded fluorophore phantom of FIG. 8 with the use of a CW methodology and the ATD methodology, respectively. Objects marked G have lifetimes of $\tau_1$=0.4 ns; objects marked R have lifetimes of $\tau_2$=1.0 ns Areas marked O indicate areas of image overlap in which the different objects are not necessarily well resolved.

In yet another experiment was based on a fluorophore phantom embedded into the hosting medium. FIG. 8 provides a corresponding schematic diagram. Here, a tube 810 containing a fluorescent medium with a lifetime of $\tau_2=1.0$ ns, is embedded inside a host medium 820 with a lifetime of $\tau_1=0.4$ ns. Both objects are shown submerged in an 88-mm-diameter culture dish 830. FIGS. 9A and 9B provide the results of reconstructions of an image of the embedded fluorophore phantom 810 with the use of a CW methodology and the ATD methodology, respectively. Objects marked G have lifetimes of $\tau_1=0.04$ ns; objects marked R have lifetimes of $\tau_2=1.0$ ns. Areas marked O indicate areas of image overlap in which the different objects are not necessarily well resolved with respect to the lifetime(s) of corresponding objects. The results convincingly demonstrate that the ATD method of reconstruction is substantially advantageous over the CW-method of reconstruction. The ability to resolve overlapping fluorophores shown in FIGS. 7 and 8 is applicable in such situations as distinguishing a tumor (or other disease target) from the background tissue. This can be achieved by designing fluorophores that change their lifetime upon binding to the tumor (or other target) (see for example Goergen et. al., *J. Biomed. Opt.* 17, 056001, 2012), so that the same methodology as in FIG. 7 and FIG. 8 can be applied to separate the tumor or other target based on lifetime differences from the background.

It is appreciated, therefore, that embodiments of the invention provide the approach for increasing a spatial resolution of optical detection carried out with an optical tomography system.

The method of the approach was disclosed to include a step of optical detection of fluorescent light, emitted by at least one irradiated fluorophore that have been placed inside a turbid medium, to obtain, for at least one source-detector pair of the system and corresponding lifetimes of said at least one irradiated fluorophore, a first one-dimensional (1D) optical data vector representing fluorescence temporal point spread functions (TPSFs) of said at least one irradiated fluorophore for a first number of early time-windows. Additionally, for at least one source-detector pair of the system, a second 1D optical data vector representing decay amplitudes of said at least one fluorophores for a second number of late time-windows is being determined as a result of the same optical detection. A third 1D optical data vector is then formed by concatenating the first and second 1D optical data vectors. To calculate the sought-after yield distribution of fluorophores, a weight matrix is defined based on (i) time-domain sensitivity functions corresponding to the first one-dimensional optical data vector and (ii) a block diagonal matrix containing continuous-wave sensitivity matrices corresponding to the decay amplitudes. A fourth 1D optical vector representing fluorescence yield distribution of the at least one irradiated fluorophore in the turbid medium is then determined based on the third 1D optical data vector and the weight matrix. In one implementation, a weight matrix may include time-domain sensitivity functions structured to map locations of points in the turbid medium to the TSPFs and/or the block diagonal matrix structured to map locations of points in the turbid medium to the decay amplitudes. Alternatively or in addition, a weight matrix may include a block diagonal matrix that contains continuous wave sensitivity matrices evaluated with the use of background absorption, of said turbid medium, that has been reduced by amounts proportional to said corresponding lifetime. The process of determining a fourth 1D optical vector may include solving, with a programmable processor, a matrix equation expressing the third 1D vector as a product of the weight matrix and the fourth 1D optical vector. Moreover, the method may require irradiating the multiple fluorophores with light produced by a pulsed source of light and collecting the optical data with the use of multiple source-detector pairs, at least some of which pairs, in one embodiment, may include a corresponding optical fiber. The process of detection of light emitted by first and second fluorophores may include detection of light from fluorophores having different lifetimes. A number of early time-gates is defined such that an aggregate time corresponding to such early time-gates exceeds an intrinsic diffusion time-scale of the turbid medium. A method may further include a step of forming an image displaying the fourth 1D optical vector as a function of a spatial position across the turbid medium and, in particular, displaying an image in which positions of the multiple irradiated fluorophores in the sample are spatially resolved with resolution exceeding that defined by a point spread function describing optical imaging performed with the system in said turbid medium. The step of identifying spatial position may include identifying spatial positions with such a value of cross-talk (among multiple fluorophores) that is representative of the second number of the late time-gates. Generally, the optical detection can be effectuated with at least one of a time-gated optical detector, a time-resolved optical detector, and a time-correlated optical detector. In a specific implementation, the optical tomography system is configured as a lifetime time-domain fluorescent tomography system.

A disclosed optical tomography system, configured for imaging a turbid sample, contains a pulsed laser source configured to irradiate the sample; and an optical system disposed to deliver and collect light, delivered from the pulsed laser source that has interacted with the sample. Such optical system including at least one (and preferably multiple) source-detector pair optically cooperated with the sample. An optical detector from the at least one source-detector pair being positioned such as to detect fluorescent light, emitted by at least one irradiated fluorophore that have been placed inside the turbid sample, for lifetime corresponding to the at least one irradiated fluorophore. The tomography system further includes a programmable processor, operably coupled with tangible non-transitory storage medium and programmed to collect optical data from the optical detector and to form, based on processing of collected optical data, a) a first one-dimensional (1D) optical data vector representing fluorescence temporal point spread functions (TPSFs) of the at least one irradiated fluorophore for a first number of early time-windows; b) a second 1D optical data vector representing decay amplitudes of said at least one fluorophores for a second number of late time-windows; c) a third 1D optical data vector by concatenating the first and second 1D optical data vectors. The optical tomography system produces fluorescence yield distribution data representing the at least one irradiated fluorophore in the turbid medium based on the third 1D optical data vector and a weight matrix comprising (i) time-domain sensitivity functions corresponding to the first one-dimensional optical data vector and (ii) a block diagonal matrix containing continuous-wave sensitivity matrices corresponding to the decay amplitudes. The at least one source-detector pair includes either a pair of optical fibers, at least one of which is positioned to collect light from the pulsed laser source) or an optical fiber and an optical detector (where the optical fined is positioned to collect light after the light interacts with the sample). In a specific implementation, an optical tomography system is configured as a lifetime time-domain fluorescent tomography system and may include a time-gate reconstruction device configured to spatially resolve first and second (generally—multiple) fluorophores embedded in a sample that has been imaged with the optical system, all fluorophores having different lifetimes.

References throughout this specification to "one embodiment," "an embodiment," "a related embodiment," or similar language mean that a particular feature, structure, or characteristic described in connection with the referred to "embodiment" is included in at least one embodiment of the present invention. Thus, appearances of the phrases "in one embodiment," "in an embodiment," and similar language throughout this specification may, but do not necessarily, all refer to the same embodiment. It is to be understood that no portion of disclosure, taken on its own and in possible connection with a figure, is intended to provide a complete description of all features of the invention.

If the schematic flow chart diagram is included, it is generally set forth as a logical flow-chart diagram. As such, the depicted order and labeled steps of the logical flow are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow-chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Without loss of generality, the order in which processing steps or particular methods occur may or may not strictly adhere to the order of the corresponding steps shown. The invention as recited in claims appended to this disclosure is intended to be assessed in light of the disclosure as a whole.

It is appreciated that at least some of the processing steps resulting in transformation of optical data, acquired with the use of the fluorescent tomographic system, can be performed with the use of a processor controlled by instructions stored in a tangible, non-transitory storage memory. The memory may be random access memory (RAM), read-only memory (ROM), flash memory or any other memory, or combination thereof, suitable for storing control software or other instructions and data. Those skilled in the art should also readily appreciate that instructions or programs defining the functions of the present invention may be delivered to a processor in many forms, including, but not limited to, information permanently stored on non-writable storage media (e.g. read-only memory devices within a computer, such as ROM, or devices readable by a computer I/O attachment, such as CD-ROM or DVD disks), information alterably stored on writable storage media (e.g. floppy disks, removable flash memory and hard drives) or information conveyed to a computer through communication media, including wired or wireless computer networks. In addition, while the invention may be embodied in software, the functions necessary to implement the invention may optionally or alternatively be embodied in part or in whole using firmware and/or hardware components, such as combinatorial logic, Application Specific Integrated Circuits (ASICs), Field-Programmable Gate Arrays (FPGAs) or other hardware or some combination of hardware, software and/or firmware components.

While the invention is described through the above-described exemplary embodiments, it will be understood by those of ordinary skill in the art that modifications to, and variations of, the illustrated embodiments may be made without departing from the inventive concepts disclosed herein. Disclosed aspects, or portions of these aspects, may be combined in ways not listed above. Accordingly, the invention should not be viewed as being limited to the disclosed embodiment(s).

What is claimed is:

1. A method for increasing a spatial resolution of optical detection carried out with an optical tomography system, the method comprising:
    with a optical detector, detecting fluorescent light; emitted by at least one irradiated fluorophore that have been placed inside a turbid medium, to obtain, for at least one source-detector pair of the system and corresponding lifetimes of said at least one irradiated fluorophore:
        a first one-dimensional (1D) optical data vector representing fluorescence temporal point spread functions (TPSFs) of said at least one irradiated fluorophore for a first number of early time-windows, and
        a second 1D optical data vector representing decay amplitudes of said at least one fluorophores for a second number of late time-windows;
    with a computer processor, disposed in operable communication with the optical detector:
        forming a third 1D optical data vector by concatenating the first and second 1D optical data vectors;
        defining a weight matrix comprising (i) time-domain sensitivity functions corresponding to the first one-dimensional optical data vector and (ii) a block diagonal matrix containing continuous-wave sensitivity matrices corresponding to the decay amplitudes;
        identifying a fourth 1D optical vector representing fluorescence yield distribution of the at least one irradiated fluorophore in the turbid medium based on the third 1D optical data vector and the weight matrix;
        transforming the fourth 1D optical vector to create at least one image showing a distribution, across the turbid medium, of said fluorescence being spatially resolved for a distinct lifetime of said at least one irradiated fluorophore.

2. A method according to claim 1, wherein the defining includes defining a weight matrix comprising time-domain sensitivity functions mapping locations of points in the turbid medium to the TSPFs.

3. A method according to claim 1, wherein the defining includes defining a weight matrix comprising the block diagonal matrix mapping locations of points in the turbid medium to the decay amplitudes.

4. A method according to claim 1, wherein the defining includes defining a weight matrix comprising a block diagonal matrix containing continuous wave sensitivity matrices evaluated with the use of background absorption, of said turbid medium, that has been reduced by amounts proportional to said corresponding lifetime.

5. A method according to claim 1, wherein said determining a fourth 1D optical vector includes solving, with a programmable processor, a matrix equation expressing the third 1D vector as a product of the weight matrix and the fourth 1D optical vector.

6. A method according to claim 1, further comprising irradiating the multiple fluorophores with light produced by a pulsed source of light.

7. A method according to claim 1, wherein the detecting includes detecting light emitted by first and second fluorophores having respectively corresponding first and second lifetimes, the first and second lifetimes being different.

8. A method according to claim 1, wherein the first number equals to a number of time- of early time-gates is defined such that an aggregate time corresponding to said first number of time-gates exceeds an intrinsic diffusion time-scale of the turbid medium.

9. A method according to claim 1, further comprising forming an image displaying said fourth 1D optical vector as a function of a spatial position across the turbid medium.

10. A method according to claim 9, wherein said forming includes distinguishing positions of the at least one irradiated fluorophore in said image with spatial resolution exceeding that defined by a point spread function that describes optical imaging with the system in said turbid medium.

11. A method according to claim 1, wherein said identifying spatial position includes identifying spatial positions with a cross-talk, among multiple fluorophores, that is representative of the second number of the late time-gates.

12. A method according to claim 1, wherein said detecting includes detecting with at least one of a time-gated optical detector, a time-resolved optical detector, and a time-correlated optical detector.

13. A method according to claim 1, carried out with a lifetime time-domain fluorescent tomography system.

14. An optical tomography system for imaging a turbid sample, the system comprising:
a pulsed laser source configured to irradiate the sample;
an optical system disposed to deliver and collect light, delivered from the pulsed laser source that has interacted with the sample, said optical system including at least one source-detector pair optically cooperated with the sample,
wherein an optical detector from the at least one source-detector pair is positioned to detect fluorescent light, emitted by at least one irradiated fluorophore that has been placed inside the turbid sample, for lifetime corresponding to the at least one irradiated fluorophore;
and
a programmable processor, operably coupled with tangible non-transitory storage medium and programmed
to collect optical data from the optical detector;
to form a first one-dimensional (1D) optical data vector representing fluorescence temporal point spread functions (TPSFs) of said at least one irradiated fluorophore for a first number of early time-windows;
to form a second 1D optical data vector representing decay amplitudes of said at least one fluorophores for a second number of late time-windows;
to form a third 1D optical data vector by concatenating the first and second 1D optical data vectors;
to output fluorescence yield distribution data representing the at least one irradiated fluorophore in the turbid medium based on the third 1D optical data vector and a weight matrix comprising (i) time-domain sensitivity functions corresponding to the first one-dimensional optical data vector and (ii) a block diagonal matrix containing continuous-wave sensitivity matrices corresponding to the decay amplitudes and
to transform said fluorescence yield distribution data to create at least one image that shows a distribution, across the sample, of fluorescence associated with the at least one irradiated fluorophore and spatially resolved for a distinct lifetime of said at least one irradiated fluorophore.

15. An optical tomography system according to claim 14, wherein the at least one source-detector pair includes a pair of optical fibers, a first fiber being positioned to deliver light from the pulsed laser source to the sample and a second fiber positioned to collect light from the pulsed laser source after it interacts with the sample.

16. An optical tomography system according to claim 14, wherein the at least one source-detector pair includes an optical fiber being positioned to deliver light from a pulsed laser source and an optical detector positioned to receive light that has traversed the optical fiber.

17. An optical tomography system according to claim 14, wherein the at least one source-detector pair includes an optical fiber positioned to collect light from the pulsed laser source and an optical detector positioned to receive light that has traversed the optical fiber.

18. An optical tomography system according to claim 14, wherein said system is a lifetime time-domain fluorescent tomography system.

19. An optical tomography system according to claim 14, including a time-gate reconstruction unit configured to spatially resolve first and second fluorophores embedded in a sample that has been imaged with the optical system, the first and second fluorophores having different lifetimes.

* * * * *